United States Patent

Neal

[11] 4,060,697
[45] Nov. 29, 1977

[54] MICROPHONE MOUNTING AND CONTROL SYSTEM

[75] Inventor: Willie Neal, Chicago, Ill.

[73] Assignee: Samuel R. Carter, Chicago, Ill. ; a part interest

[21] Appl. No.: 664,560

[22] Filed: Mar. 8, 1976

[51] Int. Cl.² .................. G05G 11/00; H04R 5/02
[52] U.S. Cl. .................. 179/1 VE; 74/481; 74/484 R; 74/491
[58] Field of Search .............. 179/1 VE, 146 R, 152, 179/153, 150; 340/22, 74; 74/481, 471, 484, 491

[56] References Cited

U.S. PATENT DOCUMENTS

| | | | |
|---|---|---|---|
| 1,785,627 | 12/1930 | Hazard | 179/1 VE |
| 2,949,044 | 8/1960 | Hughes | 74/481 |
| 3,043,912 | 7/1962 | DeLaney | 179/1 VE |
| 3,324,254 | 6/1967 | Shaw et al. | 179/150 |
| 3,344,236 | 9/1967 | Chipping | 179/1 VE |

*Primary Examiner*—William C. Cooper
*Assistant Examiner*—E. S. Kemeny
*Attorney, Agent, or Firm*—Thomas R. Vigil

[57] ABSTRACT

The system includes a holder for a microphone, a mounting structure for mounting the holder from a dashboard in the drivers compartment of a vehicle, and mechanisms for operating the microphone while operating the vehicle. The operating mechanisms include a lever arm pivotally mounted on the holder with a plate portion of the lever arm located adjacent to and spring biased outwardly from a control button extending from one side of the microphone situated in the holder, a trigger which is mountable on a control arm extending from a steering column of a vehicle and a cable connected between the trigger and the lever arm. Typically the vehicle control arm is one used by a handicapped person having limited use of his legs and includes acceleration and brake controls. The system permits a vehicle operator to operate the microphone without removing his hands from the steering wheel and control arm of the vehicle while operating the vehicle.

6 Claims, 3 Drawing Figures

MICROPHONE MOUNTING AND CONTROL SYSTEM

BACKGROUND OF THE INVENTION

The present invention relates to a microphone mounting and control system for use in the drivers compartment of a vehicle. The system of the present invention enables one to operate the microphone without releasing his hands from the steering and control devices for the vehicle. Such a system is particularly useful to a handicapped person who has little use of his legs and must maintain one hand on the steering wheel of the vehicle and the other hand on a control arm extending from a steering column of a vehicle and having acceleration and brake controls thereon, while the vehicle is in motion.

With advances in technology, various mechanisms and controls have been developed for enabling a handicapped person to operate a motor vehicle. Several examples of special control mechanisms for operating a vehicle are disclosed in the following U.S. Patents:

U.S. Pat. No. 2,602,348
U.S. Pat. No. 2,707,886
U.S. Pat. No. 2,731,850
U.S. Pat. No. 2,827,801

Since the handicapped person has limited mobility, it is desirable that such a vehicle, which is specially adapted for operation by a handicapped person, also have a two way radio system, so that, if the person is unable to continue operation of the vehicle, he can radio for assistance.

Where the handicapped person has limited use of his legs and can not operate the normal foot pedals provided in a vehicle for controlling accelerating and braking of the vehicle, a modified acceleration and brake control mechanism has heretofore been developed which includes a hand operated control arm which extends outwardly from the steering column of the vehicle. This control arm has control means such as rotatable sleeve portions by which the operator can control the acceleration and braking of the vehicle. Typically, the control arm extends from the steering column toward the door on the drivers side of the vehicle. With this arrangement, the handicapped person can operate the control arm with his left hand while holding the steering wheel with his right hand.

With both of his hands occupied, the handicapped operator of the vehicle often finds it ackward, if not impossible, to also operate a microphone, particularly while the vehicle is in motion. To solve this problem and as will be described in greater detail hereinafter, the present invention provides a microphone mounting and control system for mounting a microphone from the dashboard in the drivers compartment of a vehicle so that the microphone is located at a position within the operators normal voice range and for operating the microphone from a position adjacent a control arm extending from the steering column of the vehicle thereby to enable the driver to operate the microphone while both of the drivers hands are occupied in operating the vehicle.

SUMMARY OF THE INVENTION

According to the invention there is provided a microphone mounting and control system for use in the drivers compartment of a vehicle, said system comprising a holder for a microphone, means for supporting said holder from a dashboard of a vehicle control means on said holder for controlling operation of a microphone in said holder, trigger means for operating said control means, means for mounting said trigger means at a convenient location adjacent means for steering a vehicle and means connecting said trigger means to said control means.

DESCRIPTION OF THE PREFERRED EMBODIMENT

Figure 1:
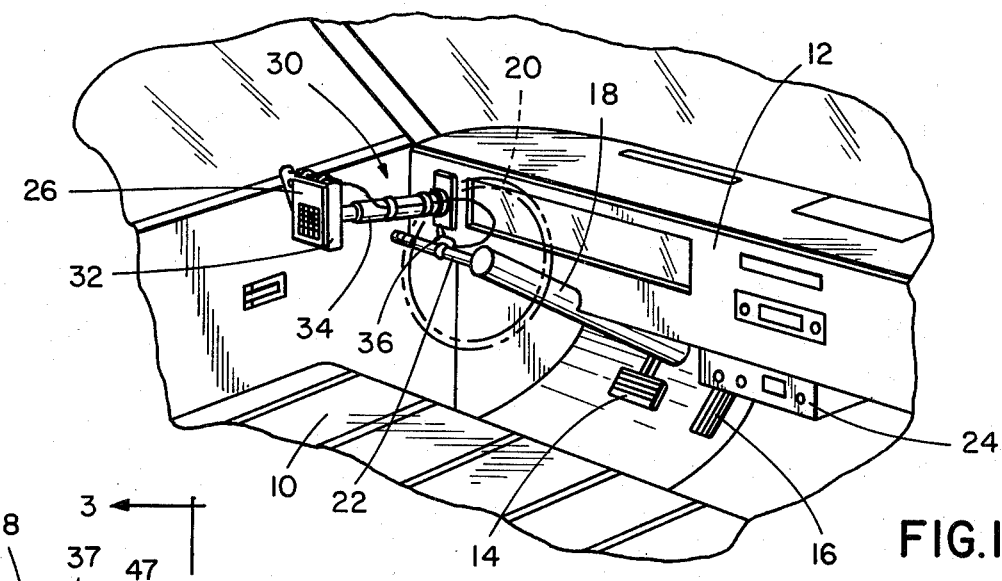
FIG. 1 is a fragmentary perspective view of the drivers compartment in a vehicle modified for use by a handicapped person having limited use of his legs and shows the microphone mounting and control system of the present invention.

Referring now to the drawings in greater detail, a drivers compartment in an automobile is illustrated in FIG. 1, and includes a drivers seat generally identified by reference numeral 10, a dashboard 12, a brake pedal 14, an acceleration pedal 16, a steering column 18 and a steering wheel 20 shown in phanom lines.

The drivers compartment shown in FIG. 1 is one which is particularly adapted for use by a handicapped person who has limited use of his legs. In this respect, in addition to the brake pedal 14 and the acceleration pedal 16, the drivers compartment has a control arm 22 which is mounted on and extends outwardly from the steering column 18. This control arm 22 is of conventional construction and includes rotatable control sleeves thereon for operating the brake mechanism and acceleration mechanism of the vehicle. Also, the drivers compartment has a two way radio 24 and a microphone 26 which is connected by conductors not shown to the radio 24.

In accordance with the teachings of the present invention, the drivers compartment has a microphone mounting and control system generally identified by the reference numeral 30. In FIG. 1 the system 30 includes a holder 32 for the microphone 26, a support arm structure 34 for mounting the holder 26 from the dashboard 12 and a trigger mechanism 36 for causing operation of the microphone 26 in the holder 32. The trigger mechanism 36 is mounted on the control arm 22 and is connected by a cable 37 to a control mechanism 38 which is associated with the holder 32 and which is operated by the trigger mechanism 36 to operate the microphone 26.

Figure 2:
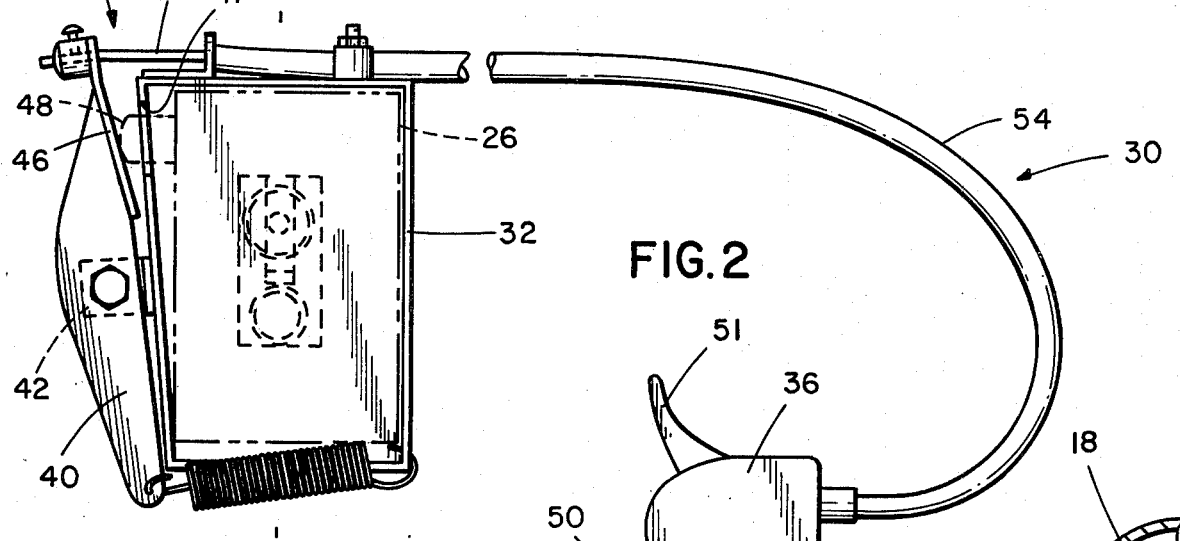
FIG. 2 is a vertical plan view with portions broken away of the microphone holder and the trigger mechanism of the system.

As shown in FIG. 2, the holder 32 is generally box shaped and is open on one side to receive the microphone 26 therein. Preferably, the holder 32 has an opening in the rear wall thereof through which a button on the microphone can extend as best shown in FIG. 3.

The control mechanism 38 includes a lever arm 40 pivotally connected intermediate the ends thereof to an ear 42 extending outwardly from one side of the holder 42. A spring 44 is connected between the lower end of the lever arm 40 and the holder 32. The upper end of the lever arm 40 has a plate 46 which is located adjacent an opening 47 in a side wall of the holder 32 through which opening 47 a button 48 of the microphone 26 can extend. As shown, the plate 46 is biased away from the microphone button 48 by the spring 44.

The trigger mechanism 36 is mounted on the control arm 22 by a clamp 50 and includes a trigger 51 connected to one end of the cable 37 which is fixed at its other end to the upper end of the lever arm 40. The cable 37 is situated within a sleeve 54 which has one end clamped to the upper side of the holder 32. In this way, when the trigger 51 is operated, the cable 37 is moved within the sleeve 54, and such movement of the cable 37 will move the plate 46 against the button 48 to actuate the microphone 26.

Figure 3:
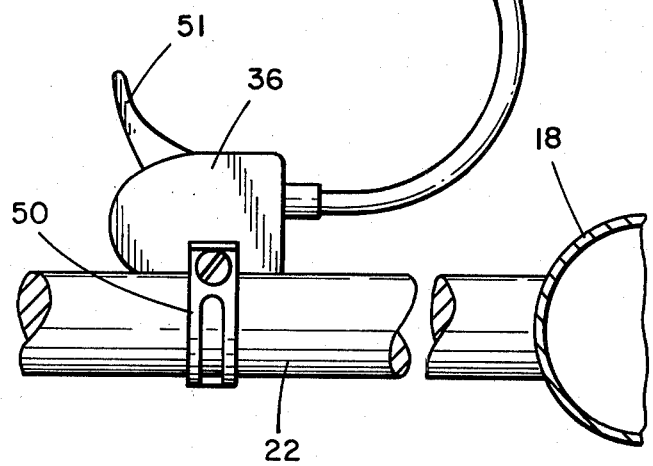
FIG. 3 is a vertical sectional view taken along line 3—3 of FIG. 2 and shows the microphone holder and the structure for mounting the holder from the dashboard of a vehicle.
Figure 3:
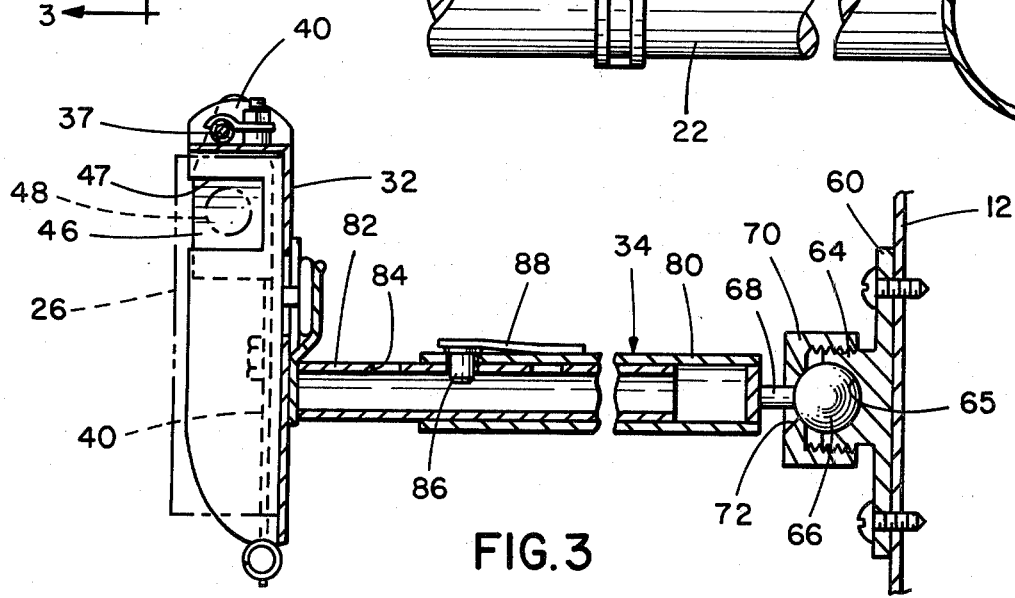

As best shown in FIG. 3, the support arm structure 34 for supporting the holder 32 from the dashboard 12 includes a mounting plate 60 which, in the illustrated embodiment, is secured by screws to a flat surface on the dashboard 12. The mounting plate 60 has a boss 61 outstanding therefrom which has a generally cylindrical threaded outer surface 64 and a semi-cylindrical socket 65 on the outer face thereof. A ball 66 secured to one end of a bar 68 is seated in the socket 65. A threaded cap 70 is positioned over the ball 66 and has a conical opening 72 therein through which the bar 68 extends. The cap 70 is threadingly received on the threaded boss 64. With this arrangement, the cap 70 can be loosened to rotate the ball 66 on the socket 65 with the conical opening 72 permitting limited pivotal movement of the bar 68.

As shown in FIG. 3, the support arm structure 34 also includes two tubular parts 80 and 82. The tubular part 80 is the larger of the two parts and is open at one end to telescopically receive the tubular part 82 therein. The other end is closed and fixed to the bar 68. The outer end of the other tubular part 82 is fixed to the back of the holder 32.

For the purpose of adjustably fixing the position of the tubular part 82 relative to the tubular part 80, the tubular part 82 has a plurality of spaced apart holes 84 therein and the tubular part 80 has a spring biased detent 86 which is receivable in one of the holes 84. The detent 86 is mounted at the end of a spring arm 88 fixed to the outer surface of the tubular part 80 and extends through an opening in the tubular part 80 so as to be in position to snap into one of the holes 84 in the tubular part 82. With this arrangement, to adjust the length of the support arm formed by the parts 80 and 82, an operator will merely pull back the spring arm 88 to move the detent 86 out of one of the holes 84 and move the tubular part 82 relative to the tubular part 80 until a desired position is obtained at which time the spring arm 88 is released to allow the detent 86 to seat in the closest hole 84.

In the operation of the microphone mounting and control system 30 of the present invention, an operator of a motor vehicle equipped with the same merely depresses the trigger 50 in order to operate the microphone 26, i.e., to turn on or turn off the microphone 26. Also, the operator can operate the trigger 50 without removing his left hand from the control arm 22 and without removing his right hand from the steering wheel 20. In this way, the operator of the vehicle can easily receive and transmit messages via the radio 28 while the automobile is in motion. Additionally, the adjustable positioning of the support arm structure, by reason of the pivotal adjustment of the bar 68 and the telescoping mounting of tubular part 82 in tubular part 80, permits easy adjustment of the microphone 26 within the normal voice range of the operator of the vehicle.

From the foregoing description it will be apparent that the microphone mounting and control system 30 of the present invention has a number of advantages some of which have been described above and others of which are inherent in the invention. Most importantly, the system 30 enables an operator of a motor vehicle to operate a microphone without removing his hands from the steering and control mechanisms for the vehicle, particularly when the vehicle is in motion.

Although a particular construction of the microphone mounting and control system 30 has been described above and illustrated in the accompanying drawing, it is to be understood that obvious modifications and variations can be made to the system 30 without departing from the spirit or scope of the invention.

Also, although the system 30 has been particularly described with reference to its use in the drivers compartment of an automobile equipped for operation by a handicapped person with limited use of his legs, it is to be understood that the system 30 can be used in other vehicles such as trucks, buses, and particularly the drivers compartment of a radio equipped taxi cab.

Accordingly, the scope of the invention is only to be limited as necessitated by the accompanying claims.

I claim:

1. Microphone mounting and control system for use in the driver's compartment of a vehicle especially adapted for operation by a handicapped person, said system being operable during operation of a vehicle and comprising a holder for a microphone, said holder having an opening in the side thereof through which a control button on a microphone positioned in said holder can extend, means for supporting said holder from a dashboard of a vehicle and at a location within the normal voice range of an operator of the vehicle, mechanical control means on said holder for engaging the control button of a microphone in said holder, trigger means for operating said mechanical control means to depress the control button, means for mounting said trigger means on an acceleration and brake control arm extending from a steering column for steering a vehicle and means connecting said trigger means to said mechanical control means.

2. The system according to claim 1, wherein said supporting means includes a mounting plate fixable to a dashboard of a vehicle and a support arm connected to and between said holder and said mounting plate.

3. The system according to claim 2, wherein said support arm has an adjustable connection to said mounting plate which permits limited pivotal adjustment of said support arm relative to said mounting plate thereby to permit vertical and horizontal adjustments of the position of said holder.

4. The system according to claim 2, including means for adjusting the length of said support arm.

5. The system according to claim 1, wherein said mechanical control means includes a lever arm which is pivotally connected to said holder and which has a plate portion located adjacent to, and spring biased outwardly from, said opening in said holder.

6. The system according to claim 5, wherein said connecting means includes a cable between said trigger means and said lever arm.

* * * * *